(12) United States Patent
Yagodkin et al.

(10) Patent No.: US 8,779,194 B2
(45) Date of Patent: Jul. 15, 2014

(54) CARBAMOYLATION OF AMINES, THIOPHENOLS, MERCAPTANES AND PHENOLS EMPLOYING ORGANIC AZIDES

(75) Inventors: Andrey Yagodkin, Kuopio (FI); Alex Azhayev, Siilinjärvi (FI)

(73) Assignee: Metkinen Chemistry Oy, Kuusisto (FI)

( * ) Notice: Subject to any disclaimer, the term of this patent is extended or adjusted under 35 U.S.C. 154(b) by 1327 days.

(21) Appl. No.: 12/447,203

(22) PCT Filed: Oct. 25, 2007

(86) PCT No.: PCT/FI2007/050575
§ 371 (c)(1),
(2), (4) Date: Apr. 24, 2009

(87) PCT Pub. No.: WO2008/049972
PCT Pub. Date: May 2, 2008

(65) Prior Publication Data
US 2010/0093981 A1     Apr. 15, 2010

Related U.S. Application Data

(60) Provisional application No. 60/854,721, filed on Oct. 27, 2006.

(30) Foreign Application Priority Data

Mar. 12, 2007 (FI) ..................................... 20075169

(51) Int. Cl.
| | |
|---|---|
| C07C 273/18 | (2006.01) |
| C07C 269/02 | (2006.01) |
| C07C 263/00 | (2006.01) |
| C07C 327/38 | (2006.01) |
| C07C 247/00 | (2006.01) |
| C07C 321/00 | (2006.01) |
| C07C 39/00 | (2006.01) |
| C07C 333/02 | (2006.01) |

(52) U.S. Cl.
CPC ......... C07C 273/1827 (2013.01); *C07C 269/02* (2013.01); *C07C 333/02* (2013.01); C07C 263/00 (2013.01); *C07C 247/00* (2013.01); *C07C 321/00* (2013.01); *C07C 39/00* (2013.01)

USPC ............... 564/32; 560/132; 560/343; 562/27; 552/1; 568/61; 568/716

(58) Field of Classification Search
USPC ......... 564/32; 560/343, 132; 562/27; 568/61, 568/716; 552/1
See application file for complete search history.

(56) References Cited

U.S. PATENT DOCUMENTS

| | | | |
|---|---|---|---|
| 3,714,217 A | 1/1973 | Sturm et al. | |
| 4,086,246 A | 4/1978 | Toth et al. | |

(Continued)

FOREIGN PATENT DOCUMENTS

| | | | |
|---|---|---|---|
| WO | WO-94/25477 A2 | 11/1994 | |
| WO | WO-2005-061445 A1 | 7/2005 | |
| WO | WO-2005/061445 A1 | 7/2005 | |

OTHER PUBLICATIONS

Cabal et al. "Total Synthesis of Calicheamicinone: A Solution to the Problem of the Elusive Urethane", Journal of the American Chemical Society 1990, vol. 112, No. 8, p. 3253-3255.

(Continued)

*Primary Examiner* — Jafar Parsa
*Assistant Examiner* — Amy C Bonaparte
(74) *Attorney, Agent, or Firm* — Birch, Stewart, Kolasch & Birch, LLP

(57) ABSTRACT

The present invention relates to carbamoylation of amines, mercaptanes, thiophenols and phenols employing organic azides. More specifically, the invention relates to a method for generating urea derivatives, thiocarbamate derivatives and carbamate derivatives, and is based on the intermediate formation of isocyanate, starting from an organic azide. The reaction as described is useful in applications for modified nucleoside synthesis, oligonucleotide synthesis, as well as modification, labeling and conjugation of polymers and biomolecules.

13 Claims, 4 Drawing Sheets

(56) References Cited

U.S. PATENT DOCUMENTS

| | | | |
|---|---|---|---|
| 4,935,413 | A | 6/1990 | Urano et al. |
| 6,300,456 | B1 | 10/2001 | Musa |
| 6,770,754 | B2 | 8/2004 | Azhayev et al. |
| 7,060,845 | B2 | 6/2006 | Guichard et al. |

OTHER PUBLICATIONS

Daiss et al., "β-Carbonylsilanes with a silacyclohexane skeleton and additional C-functionalized organyl groups at the silicon atom: synthesis, reactivity, and NMR-spectroscopic characterization", Journal of Organometallic Chemistry, 2005, vol. 690, No. 3, p. 678-684.

Sakurai et al., "DNA-Templated Functional Group Transformations Enable Sequence-Programmed Synthesis Using Small-Molecule Reagents", J. Am. Chem. Soc. 2005, vol. 127, p. 1660-1661.

Menuel et al., "New synthetic approach to per-O-acetyl-isocyanates, isothiocyanates and thioureas in the disaccharide and cyclodextrin series", New Journal of Chemistry, 2006, vol. 30, pp. 603-608.

Kovacs et al., "A New Route to Cyclic Urea Derivatives of Sugars via Phosphinimines", Carbohydrate Research, vol. 166 (1987), pp. 101-111.

Eguchi et al., "Synthesis of novel carbo- and heteropolycycles. VI. Reactions of some bridgehead- and bridge-azides related to adamantane with some selected trivalent phosphorus compounds", Nippon Kagaku Kaishi (1987), (7), p. 1280-1283, STN International, Acc. No. 108:149952.

Jager et al., "Carbamates and Carbamoyl Chlorides", teoksessa Ullmann's Encyclopedia of Industrial Chemistry, Sixth, Completely Revised Edition, Weinheim, WILEY-VCH Verlag GmbH & Co. KGaA, 2003, ISBN 3-527-30385-5, vol. 6, pp. 207-209.

Meessen et al., "Urea", teoksessa Ullmann's Encyclopedia of Industrial Chemistry, Sixth, Completely Revised Edition, Weinheim, WILEY-VCH Verlag GmbH & Co. KGaA, 2003, ISBN 3-527-30385-5, vol. 37 pp. 683 & 708.

Paul, F. "Catalytic synthesis of isocyanates or carbamates from nitroaromatics using Group VIII transition metal catalysts" Coordination Chemistry Reviews, 2000, vol. 203, pp. 269-323.

Valli, V.L.K., et al., "A Simple, Convenient, and Efficient Method for the Synthesis of Isocyanates from Urethanes". Journal of Organic Chemistry published by the American Chemical Society, 1995, vol. 60, pp. 257-258.

Braverman, S. et al., A Novel Synthesis of Isocyanates and Ureas via β-Elimination of Haloform Tetrahedron Letters, vol. 40 (1999), pp. 3235-3238.

Azhayev, A, V., et al., "Amide group assisted 3'-dephosphorylation of oligonucleotides synthesized on universal A-supports". Tetrahedron, vol. 57 (2001), pp. 4977-4986.

Atkinson, T., et al, "Oligonucleotide synthesis: practical approach" IRL Press, Oxford, 1984, pp. 45-49.

Woods, G., "The ICI Polyrethanes Book", Polyurethanes and John Wiley & Sons, second edition, (1990), pp. 10-12 and 32-35.

13a: Base = Ade; 13b: Base = Gua;
13c: Base = Ura; 13d: Base = Cyt

CARBAMOYLATION OF AMINES, THIOPHENOLS, MERCAPTANES AND PHENOLS EMPLOYING ORGANIC AZIDES

The present application is a national phase application filed under 35 U.S.C. §371 based on PCT/FI2007/050575 filed on Oct. 25, 2007. PCT/FI2007/050575 claims priority to U.S. Provisional Application No. 60/854,721 filed Oct. 27, 2006 and to Application No. 20075169 filed in Finland on Mar. 12, 2007 under 35 U.S.C. §119(a) and (e), the entire contents of the above-described applications are hereby incorporated by reference.

FIELD OF THE INVENTION

The present invention relates to carbamoylation of amines, mercaptanes, thiophenols and phenols employing organic azides. More specifically, the invention relates to a method for generating urea derivatives, thiocarbamate derivatives and carbamate derivatives, and is based on the intermediate formation of isocyanate, starting from an organic azide. The reaction as described is useful in applications for modified nucleoside synthesis, oligonucleotide synthesis, as well as modification, labeling and conjugation of polymers and biomolecules.

BACKGROUND OF THE INVENTION

International patent application No. WO 2005/061445 (Langstrom et al.) (1) and references cited therein are describing carbonylation via isocyanate using azides and carbon monoxide. This reaction is promoted by a transition metal complex (e.g rhodium, palladium) and is performed in a high pressure reaction chamber. The main features of Langstrom's and similar methods are as follows: Introduction of carbon monoxide into the reaction chamber via the gas inlet and introduction at high pressure an azide solution mixed with a transition metal complex and a liquid reagent (solvent) into the reaction chamber via the liquid inlet. Since Langstrom method is dealing with carbon-isotope monoxide, additional technical measures have to be undertaken for trapping the carbon-isotope dioxide and converting it to carbon-isotope monoxide.

Obviously, these reactions require very special equipment, alkyl azide solution, expensive transition metal complex and hazardous highly toxic gas—carbon monoxide.

In contrast to this kind of procedure, the present method utilizes an alkyl azide solution, inexpensive compound of trivalent phosphorous (e.g. triphenylphosphine) and trialkylammonium hydrogen carbonate buffer. This buffer is prepared by simple bubbling of harmless carbon dioxide in a mixture of trialkylamine and water until pH about 7-8 is reached. The carbamoylation reaction itself is then performed in a tightly closed vessel, like, e.g, a bottle with a screw cap.

It is noteworthy that the present procedure is extremely simple. It does not require any special equipment (unlike Langstrom's (1) or similar procedures), any expensive transition metal complexes or, more importantly, a hazardous highly toxic gas—carbon monoxide. In other words, the present procedure may be carried out in any chemical laboratory.

SUMMARY OF THE INVENTION

The present invention relates to a straightforward method of carbamoylation of amines, mercaptanes, thiophenols and phenols, employing an organic azide, a compound of trivalent phosphorous, an aqueous trialkylammonium hydrogen carbonate buffer and an organic solvent. This method may be successfully employed in basic organic chemistry, and also for the synthesis of various nucleoside derivatives and modification of various particles and solid surfaces.

DETAILED DESCRIPTION OF THE INVENTION

Abbreviations

Figure 1:
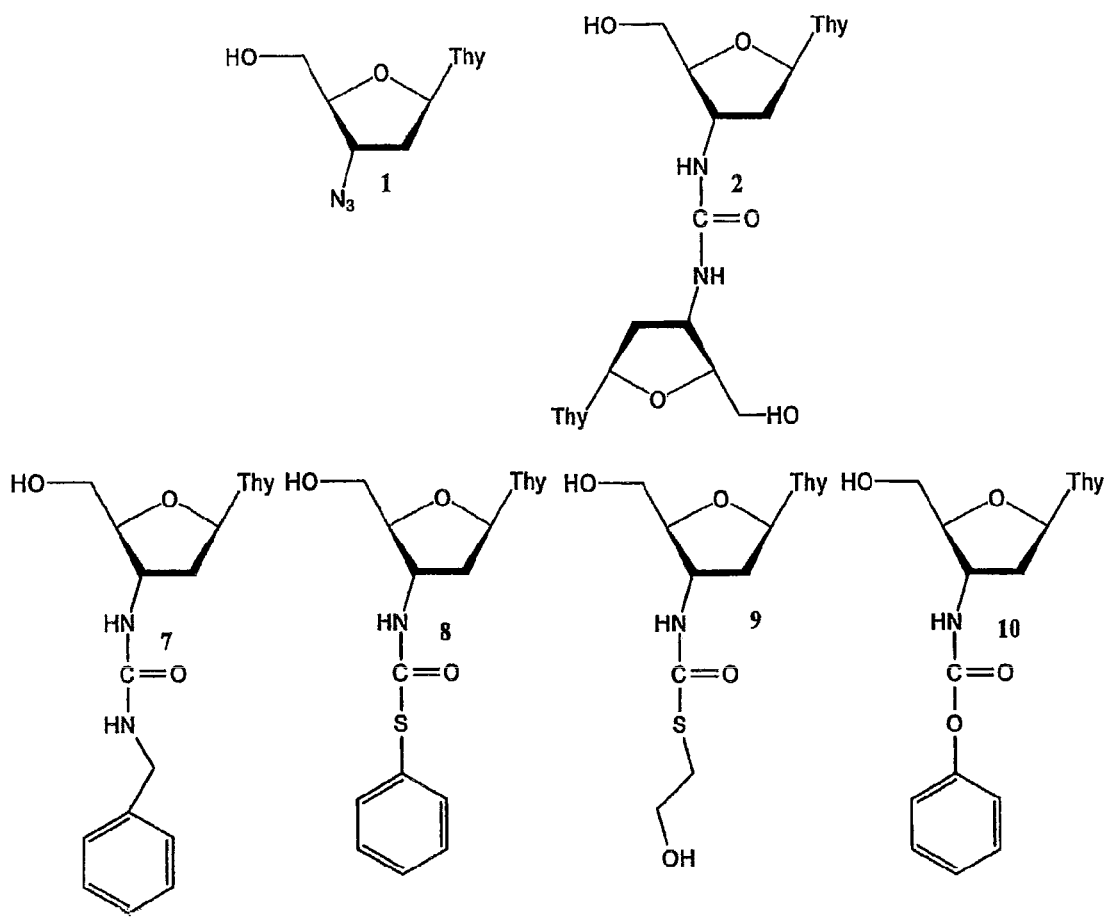
FIG. 1 shows transformations of 3'-azido-3'-deoxythymidine.

Ade Adenin-9-yl
AMPS Macroporous Aminomethyl Polystyrene
CPG Controlled Pore Glass
Cyt Cytosin-1-yl
DMTr 4,4'-Dimethoxytriphenylmethyl
Gua Guanin-9-yl
Fmoc 9-Fluorenylmethoxycarbonyl
$N^6$-Bz-Ade $N^6$-Benzoyl-Adenin-9-yl
$N^4$-Bz-Cyt $N^4$-Benzoyl-Cytosin-1-yl
$N^2$-ibu-Gua $N^2$-isobutyryl-Guanin-9-yl
Thy Thymin-1-yl
Ura Uracil-1-yl
USIII Universal Solid Support III The present invention relates to the reaction of carbamoylation of amines Ia, mercaptanes Ib, thiophenols Ic or phenols Id, employing organic azides II (Scheme 1). The reaction proceeds via intermediate formation of isocyanates of general formulae III and results in products of general formulae IV.

Basic chemistry of various transformations mentioned herein is depicted as follows from Scheme 2.

The organic group R in Schemes 1 and 2 may be any organic group capable of forming an organic azide compound. Consequently, R may be linear or cyclic lower alkyl, which may optionally be substituted, arylalkyl, aminoalkyl, or lower alcohol. R may also be nucleosidyl, nucleotidyl, oligonucleotidyl or peptidyl, as well as ribosyl, 2'-deoxyribosyl or any functional derivative thereof. In any of the mentioned organic groups any functional group may be protected, if appropriate. Preferably R is lower aminoalkyl or nucleosidyl, more preferably 3-aminopropyl or 3'-deoxythymidilyl.

R' as an aliphatic organic group is preferably linear or cyclic lower alkyl, which is optionally substituted, or deoxynucleosidyl. R' is in this case, for instance, hydroxyethyl.

R' as an aromatic organic group is preferably aryl or substituted aryl. R' is in this case, for instance, phenyl or benzyl.

The method of synthesis described in the present application comprises reduction of organic azides II with a compound of trivalent phosphorous (triphenylphosphine, trialkylphosphine, trialkylphosphite, hexaalkyltriamidophosphite, etc.) in an organic solvent (1,4-dioxane, tetrahydrofurane, acetonitrile, etc.) in the presence of hydrogen carbonate ions (various trialkylammonium hydrogen carbonate buffers, e.g. trimethylammonium hydrogen carbonate, triethylammonium hydrogen carbonate, diethyl-2-hydroxyethylammonium hydrogen carbonate, etc.), leading to formation of intermediate structures incorporating —P=N— function, followed by formation of isocyanates III and finally by reaction with amines, mercaptanes, thiophenols or phenols as nucleophiles to give rise to ureas IVa, thiocarbamates IVb and IVc or carbamates IVd.

The procedure to generate substituted ureas IVa, thiocarbamates IVb,c and carbamates IVd is the preferred method of the present invention by virtue of its broad employment for synthesis and modification of various organic compounds.

Since the intermediate reactive product of this reaction is an isocyanate of structure III, the present invention may be successfully utilized in chemical synthesis and chemical industry, where generation of isocyanates is required or where isocyanates serve as starting compounds. The present invention discloses a procedure which complements a number of contemporary methods of synthesis and manufacture of isocyanates (2, 3, 4, 5).

The procedure is a highly effective and simple new conjugation reaction that is complementing conventional methods of bioconjugation. It is applicable in diverse areas including applications for oligonucleotide synthesis, modification and conjugation. More broadly it may find use in nanotechnology, arrays, diagnostics and screening assays. The technique can be readily engineered to link small molecules (peptides, fluorophores, oligonucleotides, etc.), biomolecules (proteins, DNA, RNA, antibodies), or other molecules to solid surfaces (beads, glass, plastic, latex), for applications in proteomics, genomics, drug discovery, diagnostics and therapeutics. The present invention will also enable the development of new applications in both genomics and proteomics that cannot be satisfied with current conventional methods.

Advantages of the present technology include:
simple and easy-to-use protocol;
carrying out the reactions at room temperature in an organic solvent containing aqueous buffered media and yielding a high-efficiency conjugation;
obtaining conjugates which have extended stability.

Consequently, the present invention may be utilized in processes in which generation of isocyanates is required or where isocyanates serve as starting compounds to react with aminoalkyl, mercaptoalkyl, thiophenylalkyl and hydroxyphenylalkyl functions.

In more detail, the present invention allows to generate the above-mentioned structures as bridges for:
conjugation of molecules bearing azidoalkyl tethers with molecules bearing aminoalkyl, mercaptoalkyl, thiophenylalkyl or hydroxyphenylalkyl groups;
conjugation of molecules bearing aminoalkyl, mercaptoalkyl, thiophenylalkyl or hydroxyphenylalkyl tethers with molecules bearing azidoalkyl groups;
conjugation of nucleosides, nucleotides and oligonucleotides bearing azidoalkyl tethers with various molecules bearing aminoalkyl, mercaptoalkyl, thiophenylalkyl or hydroxyphenylalkyl groups (luminescent and spin labels, various chelates, modified peptides, modified proteins, modified antibodies, etc.);
conjugation of nucleosides, nucleotides and oligonucleotides bearing azidoalkyl tethers with peptides, proteins, antibodies, etc.;
conjugation of molecules (luminescent and spin labels, various chelates, etc.) bearing azidoalkyl tethers with peptides, proteins, antibodies, etc.;
conjugation of nucleosides, nucleotides and oligonucleotides bearing aminoalkyl, mercaptoalkyl, thiophenylalkyl or hydroxyphenylalkyl tethers with various molecules bearing azidoalkyl groups (luminescent and spin labels, various chelates, modified peptides, modified proteins, modified antibodies, etc.);
conjugation of oligonucleotides bearing aminoalkyl, mercaptoalkyl, thiophenylalkyl or hydroxyphenylalkyl tethers with solid phase bearing azidoalkyl groups to prepare oligonucleotide arrays, oligonucleotide-bound microparticles, nanoparticles, etc.;
conjugation of oligonucleotides bearing azidoalkyl tethers with solid phase bearing aminoalkyl, mercaptoalkyl, thiophenylalkyl and hydroxyphenylalkyl groups to prepare oligonucleotide arrays, oligonucleotide-bound microparticles, nanoparticles, etc.;
conjugation of protected nucleosides bearing azidoalkyl tethers with various solid matrices (controlled pore glass, polystyrene, polyvinylacetate) bearing aminoalkyl, mercaptoalkyl, thiophenylalkyl or hydroxyphenylalkyl groups to prepare nucleoside-bound solid supports for DNA, RNA and modified oligonucleotide solid phase synthesis;
conjugation of protected nucleosides bearing aminoalkyl, mercaptoalkyl, thiophenylalkyl and hydroxyphenylalkyl tethers with various solid matrices (controlled pore glass, polystyrene, polyvinylacetate) bearing azidoalkyl groups to prepare nucleoside-bound solid supports for DNA, RNA and modified oligonucleotide solid phase synthesis;
conjugation of specific molecules bearing azidoalkyl tethers with various solid matrices (controlled pore glass, polystyrene, polyvinylacetate) bearing aminoalkyl, mercaptoalkyl, thiophenylalkyl and hydroxyphenylalkyl groups to prepare universal solid supports for DNA, RNA and modified oligonucleotide solid phase synthesis;
conjugation of specific molecules bearing aminoalkyl, mercaptoalkyl, thiophenylalkyl and hydroxyphenylalkyl tethers with various solid matrices (controlled pore glass, polystyrene, polyvinylacetate), bearing azidoalkyl groups to prepare universal solid supports for DNA, RNA and modified oligonucleotide solid phase synthesis.

EXAMPLES 1. 3'-Azido-3'-deoxythymidine derivatives

Example 1

3'-Azido-3'-deoxythymidine (1, 0.37 mmol) was added to a solution of triphenylphosphine (0.4 mmol) in a mixture of dioxane (4 ml) and 1M aqueous triethylammonium hydrogen carbonate (0.5 ml). The mixture was left for 24 hours at room temperature and evaporated to dryness. Chromatographic separation on silica gel afforded dimer 2 (FIG. 1) in 53% yield.

Example 2

3'-Azido-3'-deoxythymidine (1, 0.37 mmol) was added to a solution of 1 mmol of compound benzylamine (3) or thiophenol (4) or mercaptoethanol (5) or phenol (6) and triphenylphosphine (0.4 mmol) in a mixture of dioxane (4 ml) and 1M aqueous triethylammonium hydrogen carbonate (0.5 ml). The mixture was left for 4 hours (for compounds 7-9) or for 24 hours (for compound 10) at room temperature and evaporated to dryness. Chromatographic separation on silica gel afforded compounds 7-9 in about 90% yield; compound 10 in 5% yield (FIG. 1).

Example 3

3'-Azido-3'-deoxythymidine (1, 0.37 mmol) was added to a solution of 1 mmol of compound benzylamine (3) and 1 mmol of mercaptoethanol (5) and triphenylphosphine (0.4 mmol) in a mixture of dioxane (4 ml) and 1M aqueous triethylammonium hydrogen carbonate (0.5 ml). The mixture was left for 12 hours at room temperature and analyzed with RP HPLC. The HPLC trace and integration of peaks revealed the complete conversion of azide 1 to give compounds 7 and 9 in 2:1 ratio (FIG. 1).

2. Modification of Aminonucleosides

Example 4

Figure 2:
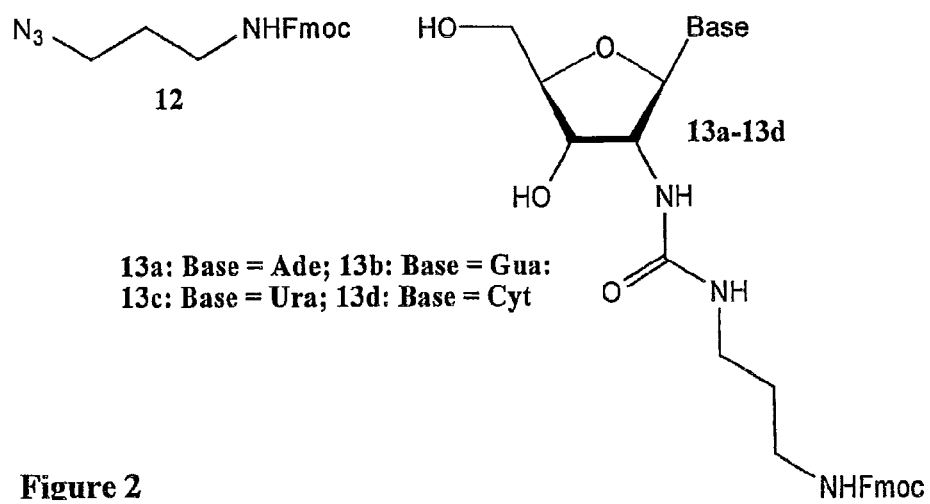
FIG. 2 shows modification of 2'-amino-2'-deoxynucleosides.

2'-Amino-2'-deoxynucleoside (11a-d, 0.37 mmol) was added to a solution of 1 mmol of azide 12 and triphenylphosphine (0.4 mmol) in a mixture of dioxane (4 ml) and 1M aqueous triethylammonium hydrogen carbonate (0.5 ml). The mixture was left for 24 hours at room temperature and evaporated to dryness. Chromatographic separation on silica gel afforded compounds 13a-d in about 80% yield (FIG. 2).

3. Modification of Particles and Solid Surfaces

A. Modification of Polystyrene and Controlled Pore Glass Based Solid Supports Resulting in Universal Solid Supports for Oligonucleotide Synthesis (6,7)

Example 5

Figure 3:
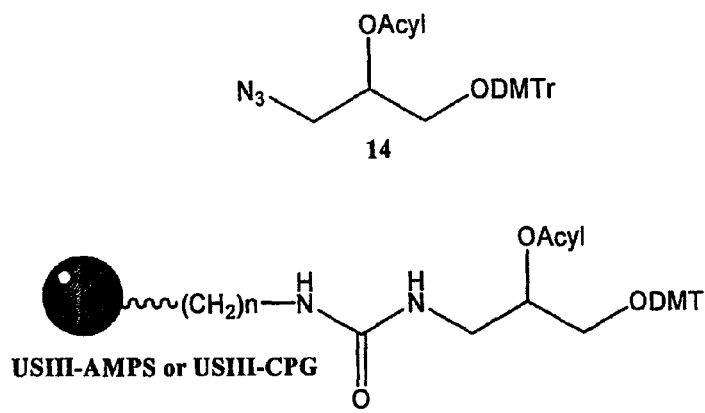
FIG. 3 shows modification of polystyrene and/or controlled pore glass based solid supports resulting in Universal Solid Supports for oligonucleotide synthesis (6,7).

A solution of azide 14 in dioxane (11.5 ml of 0.09 M solution for 0.4 mmol of linker loaded support; 23 ml of 0.09 M solution for 0.8 mmol of linker loaded support) was added to a suspension of 20 g of Macroporous Aminomethyl polystyrene (cross-linking—60%, particle size—100-200 mesh, loading of amino groups—0.12 mmol/g) in dioxane (188 ml for 0.4 mmol of linker loaded support; 177 ml for 0.8 mmol of linker loaded support). To the resulting suspension the aqueous solution of triethylammonium hydrogen carbonate (2 M, 5 ml) and triphenylphosphine (3 g for 0.4 mmol of linker loaded support; 6 g for 0.8 mmol of linker loaded support) were added and the mixture was shaken for 48 h at room temperature. The resin was filtered off, washed with acetone, followed by tetrahydrofurane and re-suspended in tetrahydrofurane (50 ml). A mixture of pyridine (70 ml) and acetic anhydride (30 ml) was then added and the resulting suspension was left for 3 h at room temperature with periodic shaking. The resin was filtered off, washed with pyridine (30 ml), acetone (200 ml), 0.1% triethylamine in ether and finally dried in high vacuum. The resulting dry resin, contained either about 0.04 mmol of DMTr-groups per gram of polymer (8)—(USIII-AMPS-40) (FIG. 3), or about 0.08 mmol of DMTr-groups per gram of polymer (8)—(USIII-AMPS-80) (FIG. 3). Both polymers, Universal Solid Supports for Oligonucleotide synthesis (USIII-AMPS-40 and USIII-AMPS-80), performed identically to the Universal Solid Support, described in detail earlier (6,7).

Example 6

A solution of azide 14 in dioxane (11.5 ml of 0.09 M solution) was added to a suspension of 20 g of Aminoalkyl Controlled Pore Glass (CPG-500: particle size—120-200 mesh, loading of amino groups—0.12 mmol/g, pore diameter 500 Å or CPG-1000: particle size—120-200 mesh, loading of amino groups—0.06-0.07 mmol/g, pore diameter 1000 Å) in dioxane (188 ml). To the resulting suspension the aqueous solution of triethylammonium hydrogen carbonate (2 M, 5 ml) and triphenylphosphine (3 g) were added and the mixture was shaken for 48 h at room temperature. The resin was filtered off, washed with acetone, followed by tetrahydrofurane and re-suspended in tetrahydrofurane (50 ml). A mixture of pyridine (70 ml) and acetic anhydride (30 ml) was then added and the resulting suspension was left for 3 h at room temperature with periodic shaking. The solid phase was filtered off, washed with pyridine (30 ml), acetone (200 ml), 0.1% triethylamine in ether and finally dried in high vacuum. The resulting dry solid phase contained: about 0.04 mmol of DMTr-groups per gram of CPG-500 (8)—USIII-CPG-500-40 (FIG. 3), or about 0.03 mmol of DMTr-groups per gram of CPG-1000 (8)—USIII-CPG-1000-30 (FIG. 3). Both solid phases, Universal Solid Supports for Oligonucleotide synthesis (USIII-CPG-500-40 and USIII-CPG-1000-30), performed identically to the Universal Solid Support, described in detail earlier (6,7).

Example 7

Figure 4:
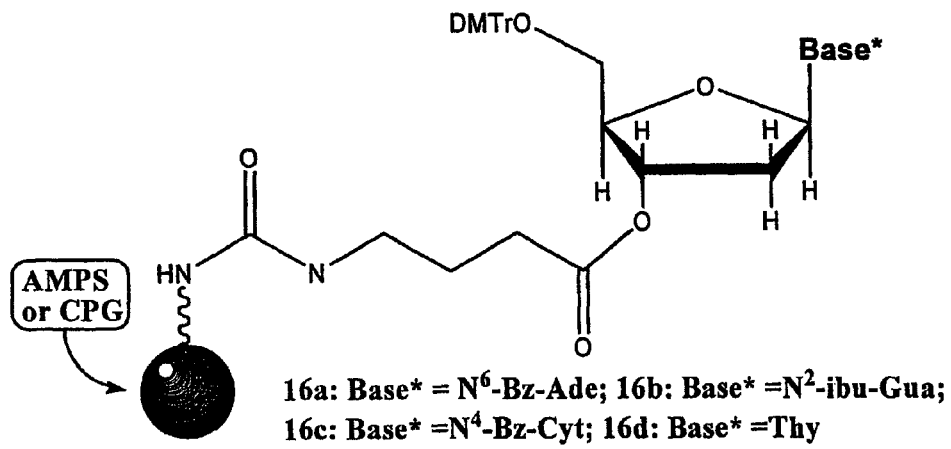
FIG. 4 shows modification of polystyrene and/or controlled pore glass based solid supports resulting in Nucleoside-bound solid supports for oligonucleotide synthesis (8).

Aminoalkyl Controlled Pore Glass (CPG-500: particle size—120-200 mesh, loading of amino groups—0.12 mmol/g, pore diameter 500 Å or CPG-1000: particle size—120-200 mesh, loading of amino groups—0.06-0.07 mmol/g, pore diameter 1000 Å) or Macroporous Aminomethyl polystyrene (cross-linking—60%, particle size—100-200 mesh, loading of amino groups—0.12 mmol/g) were derivatized with 3'-O-(4-azidobutyryl)-5'-O-dimethoxytrityl-N-acyl-nucleosides 16a or 16b or 16c or 3'-O-(4-azidobutyryl)-5'-O-dimethoxytritylthymidine 16d. Procedures for derivatization were described in Examples 4-6. The resulting dry solid phases contained 0.03-0.08 mmol of DMTr-groups per gram of solid support (8). All four nucleoside-bound solid supports 17a-d (FIG. 4) performed well in standard oligonucleotide synthesis.

B. Derivatization of Nanoparticles with Oligonucleotide

Example 8

Sigma-Aldrich 3-Aminopropyl-functionalized silica nanoparticles, 3% (w/v) in ethanol (average particle size=15 nm), 2.5 ml were evaporated to dryness and re-suspended in dioxane (1.9 ml).

Figure 5:
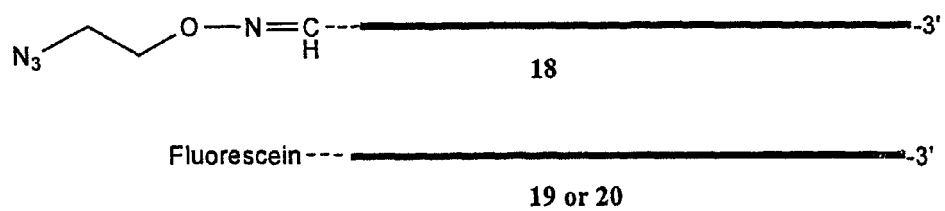
FIG. 5 schematically shows azidoalkyl-tethered synthetic oligonucleotide for subsequent attachment to solid phases and surfaces and fluorescein-labeled synthetic oligonucleotides for testing oligonucleotide-derivatized nanoparticles and microarray slides.
Figure 6:
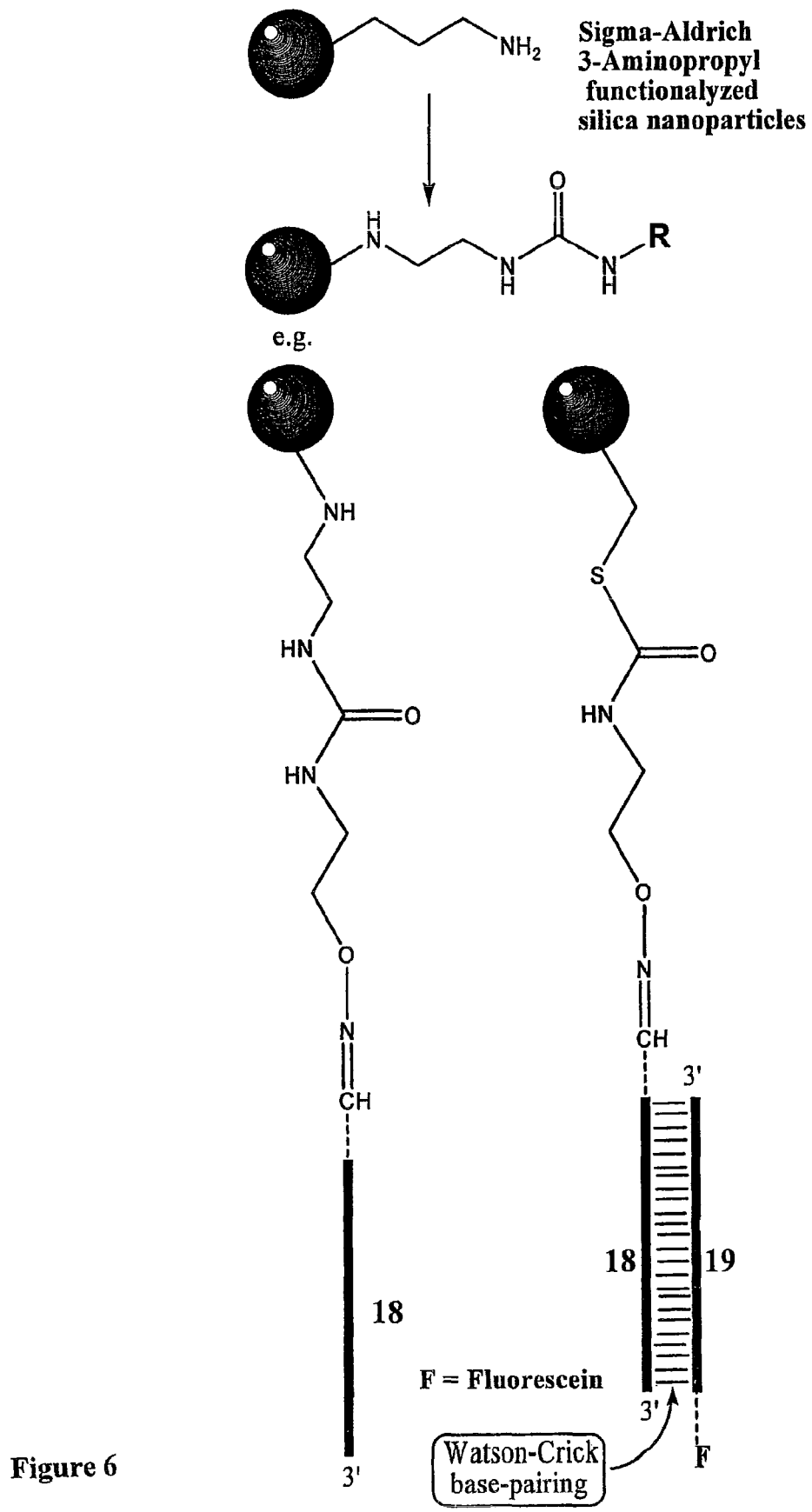
FIG. 6 shows oligonucleotide-functionalized nanoparticles.

A solution of 10 µmol of azidoalkyl-tethered oligonucleotide 18 (FIG. 5) in aqueous triethylammonium hydrogen carbonate (2 M, 0.05 ml) and triphenylphosphine (0.03 g) were added to the suspension of nanoparticles and the mixture was periodically gently shaken for 48 h at room temperature. The supernatant was removed by centrifugation. The nanoparticles were re-suspended in dioxane and the supernatant was removed by centrifugation (2 times), re-suspended in 40% aqueous ethanol and the supernatant was removed by centrifugation (2 times). The resulting oligonucleotide 18 functionalized nanoparticles (FIG. 6) were re-suspended in a buffer containing 10 mM Tris-HCl, pH 7.0; 0.1 M NaCl; 10 mM $MgCl_2$ to give 3% (w/v) and analyzed.

Fluorescein-labeled oligonucleotide 19 (FIG. 5) (oligonucleotide 19 had a sequence complementary to oligonucleotide 18, 1 µmol in 0.1 ml of buffer containing 10 mM Tris-HCl, pH 7.0; 0.1 M NaCl; 10 mM $MgCl_2$) was added to a suspension of oligonucleotide 18 functionalized nanoparticles (0.1 ml). The mixture was gently shaken for 1 h at room temperature. The supernatant was removed by centrifugation, nanoparticles were re-suspended in 40% aqueous ethanol and the supernatant was removed by centrifugation (3 times). The resulting particles were re-suspended in 80% aqueous ethanol (3% w/v). These nanoparticles were of intense green color.

Fluorescein-labeled oligonucleotide 20 (FIG. 5) (oligonucleotide 20 had a sequence non-complementary to oligonucleotide 18, 1 µmol in 0.1 ml of water) was added to a suspension of oligonucleotide 18 functionalized nanoparticles (0.1 ml). The mixture was gently shaken for 1 h at room temperature. The supernatant was removed by centrifugation, nanoparticles were re-suspended in a buffer containing 10 mM Tris-HCl, pH 7.0; 0.1 M NaCl; 10 mM $MgCl_2$ and the supernatant was removed by centrifugation (3 times). The resulting particles were re-suspended in 80% aqueous ethanol (3% w/v). These nanoparticles were of extremely pale green color.

C. Functionalization of Microarray Surface with Oligonucleotide

Example 9

Figure 7:
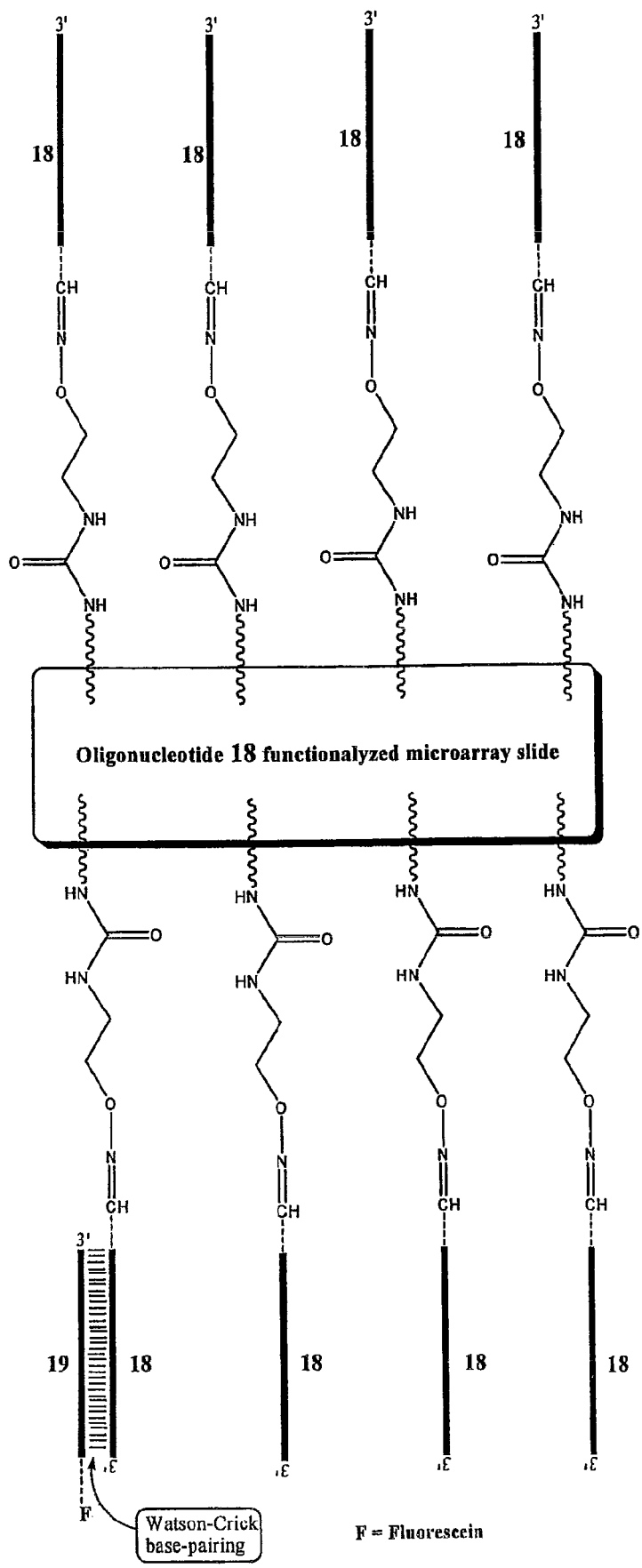
FIG. 7 shows an oligonucleotide-functionalized microarray slide.

Two Amine-derivatized slides (Erie Scientific Company) were immersed in a mixture of dioxane (1.88 ml) and aqueous triethylammonium hydrogen carbonate (2M, 0.05 ml), containing azidoalkyl-tethered oligonucleotide 18 (FIG. 5), 10 µmol. Triphenylphosphine (30 mg) was added and the slides were gently shaken for 48 h at room temperature. The oligonucleotide 18 functionalized slides (FIG. 7) were then washed with 50% aqueous ethanol (2 times), water (2 times), dioxane (2 times), ethanol (2 times) and dried.

A solution of fluorescein-labeled oligonucleotide 19 (FIG. 5) (oligonucleotide 19 had a sequence complementary to oligonucleotide 18, 1 µmol in 0.1 ml of buffer containing 10 mM Tris-HCl, pH 7.0; 0.1 M NaCl; 10 mM $MgCl_2$) was manually spotted on the first oligonucleotide 18 functionalized slide. The slide was gently shaken for 1 h at room temperature. The slide was washed with buffer containing 10 mM Tris-HCl, pH 7.0; 0.1 M NaCl; 10 mM $MgCl_2$ (3 times) water, followed by ethanol and finally dried. The resulting slide had several intense green color spots.

When oligonucleotide 20 (FIG. 5) (oligonucleotide 20 had a sequence non-complementary to oligonucleotide 18) was spotted on the second slide and subsequently washed as described for the first slide, the resulting second slide had several visible spots of extremely pale green color.

The present invention is not limited in scope by specified embodiments described herein. All additional modifications of the invention described herein and resulting from description and figures will appear apparent to those skilled in the art. All such modifications are falling within the scope of claims appended herein.

The disclosures of various cited patents and publications are incorporated herein by reference and are not falling within the scope of the claims appended herein.

REFERENCES

1. International patent application No. WO 2005/061445 (Langstrom et al., "Methods for carbon isotope labeling synthesis by rhodium-promoted carbonylation via isocyanate using azides and carbon-isotope monoxide")
2. George, W. The ICI Polyuretanes Book, Ed2, 1990, Published jointly by ICI and John Wiley & Sons, N.Y.
3. Paul, F. *Coordination Chemistry Reviews*, 2000, 203, 269-323.
4. Valli, V. L. K., Alper, H. *J. Org. Chem.* 1995, 60, 257-258.
5. Braverman, S., Cherkinsky, M., Kedrova, L., Reiselman, A. *Tetrahedron Letters*, 1999, 40, 3235-3238.
6. Azhayev, A., Antopolsky, M. *Tetrahedron*, 2001, 57, 4977-4986.
7. Azhayev, A., Antopolsky, M. U.S. Pat. No. 6,770,754 and European Patent Application No. 1 404 695.
8. Atkinson, T., Smith, M. in *Oligonucleotide Synthesis. A Practical Approach*; Gait, M. J. Ed.; IRL Press: Oxford, 1984, p. 111.

Scheme 1

$$R-N_3 \xrightarrow[\text{\& trialkylammonium hydrogen carbonate buffer}]{\text{compound of P(III)}}$$
IIa-d $$[R-N=C=O] \xrightarrow{R'-XH} R-NH-\underset{O}{\overset{\|}{C}}-X-R'$$
IIIa-d $\quad\quad\quad\quad\quad\quad\quad\quad\quad\quad\quad\quad\quad$ IVa-d where R - an organic group
and
R' = an aliphatic organic group, X = NH or NR" (Ia and IVa), where R" = alkyl;
R' = an aliphatic organic group, X = S (Ib and IVb);
R' = an aromatic organic group, X = S (Ic and IVc);
R' = an aromatic organic group, X = O (Id and IVd);
The applications of this reaction are shown as follows:

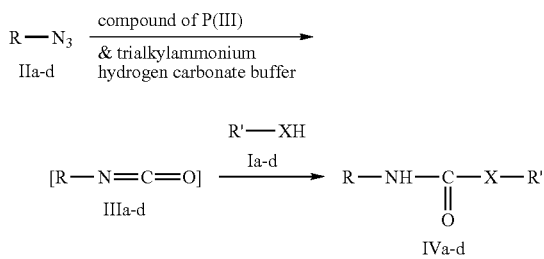

$R-N_3 \longrightarrow \longrightarrow R-NH-CO-NR'R''$
Synthesis of urea derivatives $R-N_3 \longrightarrow \longrightarrow R-NH-CO-SR'$
Synthesis of thiocarbamate derivatives $R-N_3 \longrightarrow \longrightarrow R-NH-CO-OR'$
Synthesis of carbamate derivatives Scheme 2

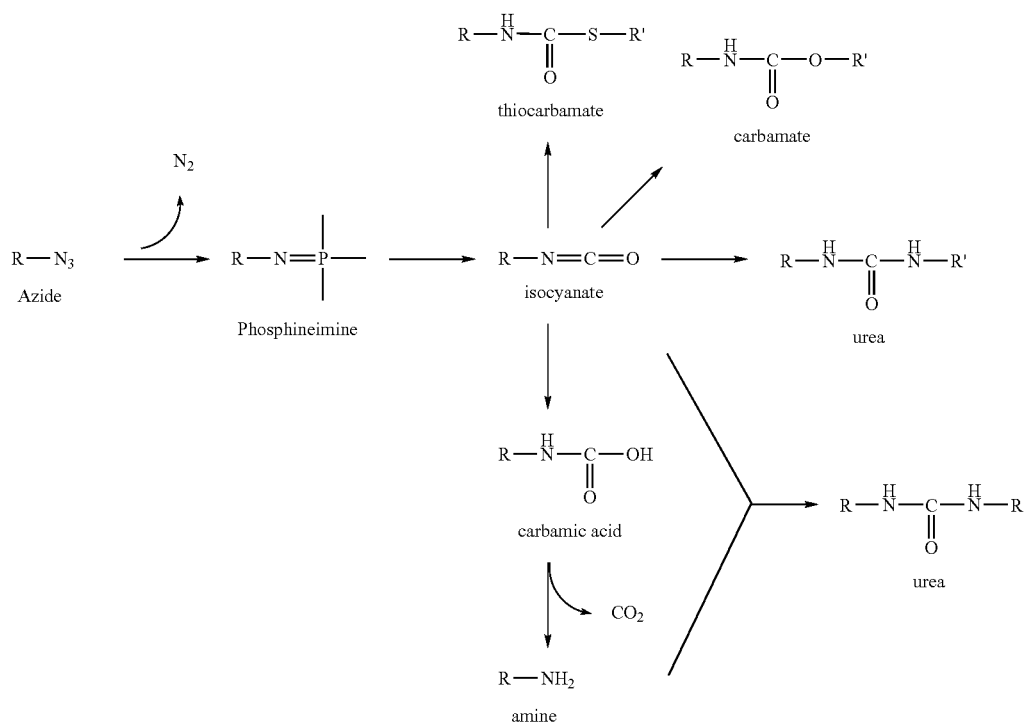

The invention claimed is:

1. A method for the preparation of a compound of formula IV

R—NH—CO—X—R'  (IV)

wherein
—R is an aliphatic or aromatic organic group, and
R' is an aliphatic organic group and X is NH; S or NR", wherein R" is alkyl; or
R' is an aromatic organic group and X is S or O,
comprising
(a) reacting a compound of formula R—N$_3$ (II), wherein R is as defined above, with a compound of trivalent phosphorous in the presence of an aqueous solution of hydrogen carbonate ions, in an organic solvent, to obtain an isocyanate of formula III

—R—N=C=O—  (III)

wherein R is as defined above, and
(b) reacting the isocyanate of formula III with a compound of formula R'—XH, wherein R' and X are as defined above,
to obtain a compound of formula IV.

2. The method according to claim 1, wherein R as an organic group is a group capable of forming an organic azide compound.

3. The method according to claim 2, wherein R is linear or cyclic lower alkyl, which may optionally be substituted, arylalkyl, aminoalkyl, lower alcohol, nucleosidyl, nucleotidyl, oligonucleotidyl, peptidyl, ribosyl or T-deoxyribosyl, in which any functional group may be protected.

4. The method according to claim 1, wherein R' as the aliphatic organic group is linear or cyclic lower alkyl, which is optionally substituted, or deoxynucleosidyl.

5. The method according to claim 1, wherein R' as the aromatic organic group is aryl or substituted aryl.

6. The method according to claim 1, wherein the compound of trivalent phosphorous is selected from the group consisting of triphenylphosphine, trialkylphosphine, trialkylphosphite and hexaalkyltriamidophospite.

7. The method according to 1, wherein the organic solvent is selected from the group consisting of 1,4-dioxane, tetrahydrofurane and acetonitrile.

8. The method according to claim 1, wherein the hydrogen carbonate ions are provided by an aqueous trialkylammonium hydrogen carbonate buffer.

9. The method according to claim 8, wherein the trialkylammonium hydrogen carbonate is selected from the group consisting of trimethylammonium hydrogen carbonate, triethylammonium hydrogen carbonate and diethyl-2-hydroxyethylammonium hydrogen carbonate.

10. The method according to claim 1 wherein X is NH or NR", for the preparation of urea derivatives.

11. The method according to claim 1 wherein X is S, for the preparation of thiocarbamate derivatives.

12. The method according to claim 1 wherein X is O, for the preparation of carbamate derivatives.

13. The method according to claim 1 for
conjugation of molecules bearing azidoalkyl tethers with molecules bearing aminoalkyl, mercaptoalkyl, thiophenylalkyl or hydroxyphenylalkyl groups;
conjugation of molecules bearing aminoalkyl, mercaptoalkyl, thiophenylalkyl or hydroxyphenylalkyl tethers with molecules bearing azidoalkyl groups;
conjugation of nucleosides, nucleotides and oligonucleotides bearing azidoalkyl tethers with luminescent and spin labels, various chelates, modified proteins and modified antibodies bearing aminoalkyl, mercaptoalkyl, thiophenylalkyl or hydroxyphenylalkyl groups;
conjugation of nucleosides, nucleotides and oligonucleotides bearing azidoalkyl tethers with peptides, proteins or antibodies;

conjugation of luminescent and spin labels and various chelates bearing azidoalkyl tethers with peptides, proteins or antibodies;

conjugation of nucleosides, nucleotides and oligonucleotides bearing aminoalkyl, mercaptoalkyl, thiophenylalkyl or hydroxyphenylalkyl tethers with luminescent and spin labels, various chelates, modified peptides, modified proteins and modified antibodies bearing azidoalkyl groups;

conjugation of protected nucleosides bearing azidoalkyl tethers with solid matrices of controlled pore glass, polystyrene or polyvinylacetate bearing aminoalkyl, mercaptoalkyl, thiophenylalkyl or hydroxyphenylalkyl groups, to prepare nucleoside-bound solid supports for DNA, RNA and modified oligonucleotide solid phase synthesis;

conjugation of protected nucleosides bearing aminoalkyl, mercaptoalkyl, thiophenylalkyl or hydroxyphenylalkyl tethers with solid matrices of controlled pore glass, polystyrene or polyvinylacetate bearing azidoalkyl groups, to prepare nucleoside-bound solid supports for DNA, RNA and modified oligonucleotide solid phase synthesis;

conjugation of oligonucleotides bearing azidoalkyl tethers with various solid matrices, including controlled pore glass, polystyrene and polyvinylacetate, bearing aminoalkyl, mercaptoalkyl, thiophenylalkyl or hydroxyphenylalkyl groups to prepare universal solid supports for DNA, RNA and modified oligonucleotide solid phase synthesis;

conjugation of oligonucleotides bearing aminoalkyl, mercaptoalkyl, thiophenylalkyl or hydroxyphenylalkyl tethers with controlled pore glass, polystyrene and polyvinylacetate solid matrices bearing azidoalkyl groups, to prepare universal solid supports for DNA, RNA and modified oligonucleotide solid phase synthesis;

conjugation of oligonucleotides bearing azidoalkyl tethers with solid matrices of silica gel, polystyrene, polyvinylacetate, micro- and nanoparticles and microarray slides, derivatized with aminoalkyl, mercaptoalkyl, thiophenylalkyl or hydroxyphenylalkyl groups;

conjugation of oligonucleotides bearing azidoalkyl tethers with solid matrices of silica gel, polystyrene, polyvinylacetate, micro- and nanoparticles and microarray slides, derivatized with aminoalkyl, mercaptoalkyl, thiophenylalkyl or hydroxyphenylalkyl groups, to prepare oligonucleotide arrays, oligonucleotide bound microparticles or nanoparticles;

conjugation of oligonucleotides bearing aminoalkyl, mercaptoalkyl, thiophenylalkyl or hydroxyphenylalkyl tethers with solid matrices of silica gel, polystyrene, polyvinylacetate, micro- and nanoparticles and microarray slides bearing azidoalkyl groups, to prepare oligonucleotide arrays, oligonucleotide-bound microparticles or nanoparticles.

\* \* \* \* \*